(12) United States Patent
Bellan et al.

(10) Patent No.: US 9,458,357 B2
(45) Date of Patent: Oct. 4, 2016

(54) PH-SENSITIVE SACRIFICIAL MATERIALS FOR THE MICROFABRICATION OF STRUCTURES

(75) Inventors: Leon M. Bellan, Somerville, MA (US);
Robert S. Langer, Newton, MA (US);
Donald M. Cropek, Champaign, IL (US)

(73) Assignees: Massachusetts Institute of Technology, Cambridge, MA (US); The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 13/410,600

(22) Filed: Mar. 2, 2012

(65) Prior Publication Data
US 2013/0066045 A1 Mar. 14, 2013

Related U.S. Application Data

(60) Provisional application No. 61/448,432, filed on Mar. 2, 2011.

(51) Int. Cl.
*C09F 1/04* (2006.01)
*C09D 193/02* (2006.01)
(Continued)

(52) U.S. Cl.
CPC .................. *C09F 1/04* (2013.01); *A61L 27/14* (2013.01); *A61L 27/56* (2013.01); *C09D 189/06* (2013.01); *C09D 193/02* (2013.01); *A61L 2400/08* (2013.01)

(58) Field of Classification Search
CPC ..... C09F 1/04; C09D 189/06; C09D 193/02; A61L 27/56; A61L 27/14

USPC ......................................................... 530/201
See application file for complete search history.

(56) References Cited

U.S. PATENT DOCUMENTS 6,977,223 B2 12/2005 George
7,192,693 B2 3/2007 Bryant
(Continued)

FOREIGN PATENT DOCUMENTS

WO      0062829    10/2000
WO   2010009320    1/2010

OTHER PUBLICATIONS

Pearnchob, N., et al. "Improvement in the distintegration of shellac-coated soft gelatin capsules in simulated intestinal fluid," J. Control. Release, 2004, 94, 313-321.*
(Continued)

*Primary Examiner* — Liam J Heincer
*Assistant Examiner* — Nicholas Hill
(74) *Attorney, Agent, or Firm* — Pabst Patent Group LLP

(57) ABSTRACT

Methods for microfabricating composite materials and composite materials prepared there from are described herein. The sacrificial material can be etched or patterned to create a two-dimensional and/or three-dimensional sacrificial material structure. The resulting sacrificial material structure can be embedded in one or more embedding materials. The sacrificial material(s) are materials whose solubility can be altered by application of a stimulus typically pH, and/or temperature, light, pH, pressure, presence of absence of ions, and combinations thereof. The embedding materials can contain one or more additives that modify one or more properties of the embedding materials, such as degradation properties, porosity, mechanical properties, viscosity, conductive properties, and combinations thereof. The composite materials can be used in tissue engineering, drug screening, toxin detection, drug delivery, filtrations, bioseparations, and as microfluidic devices for fluid mixing and structural repair.

10 Claims, 1 Drawing Sheet

(51) Int. Cl.
  A61L 27/14    (2006.01)
  A61L 27/56    (2006.01)
  C09D 189/06   (2006.01)

(56) References Cited

U.S. PATENT DOCUMENTS

| | | | |
|---|---|---|---|
| 7,425,288 | B2 | 9/2008 | Flodin |
| 2004/0226620 | A1 | 11/2004 | Therriault |
| 2006/0154485 | A1 | 7/2006 | Li |
| 2008/0206308 | A1 | 8/2008 | Jabbari |
| 2009/0236310 | A1 | 9/2009 | Linder |
| 2011/0002986 | A1* | 1/2011 | Durig et al. ............ 424/463 |

OTHER PUBLICATIONS

Sung, J. H., et al., "Microscale 3-D hydrogel scaffold for biomimetic gastrointestinal (GI) tract model," Lab Chip, 2011, 11, 389-392. Published online: Dec. 15, 2010.*
FMC BioPolymer, "Alginates," 2003.*
Voragen, A. C. J., et al., "Polysaccharides," Ullmann's Encyclopedia of Industrial Chemistry, vol. 29, 417-473. Published online: Mar. 15, 2003.*
Guidechem.com, entry for shellac. http://www.guidechem.com/dictionary/en/9000-59-3.html. Downloaded on Jan. 13, 2014.*
Titanium Dioxide MSDS. Acros Organics. 2006, 4 pages.*
Chen, et al., "pH-Sensitive Thin Hydrogel Microfabricated by Photolithography," Langmuir 1998, 14, 6610-6612.*
Gui, et al., "Fabrication of free-standing polyelectrolyte multilayer films: A method using polysulfobetaine-containing films as sacrificial layers," Journal of Colloid and Interface Science 340 (2009) 35-41.*
Metz, S., et al., "Polyimide and Su-8 microfluidic devices manufactured by heat-depolymerizable sacrificial material technique," Lab Chip, 2004, 4, 114-120.*
Stachiowiak, A., et al., "Bioactive Hydrogels with an Ordered Cellular Structure Combine Interconnected Macroporosity and Robust Mechanical Properties," Adv. Mater., 2005, 17, 399-403.*
Burg, et al., "Biomaterial developments for bone tissue engineering", Biomaterials, 21:2347-59 (2000).
Cabodi, et al., "A microfluidic Biomaterial", J Am. Chem. Soc., 127:13788-89 (2005).
Chevalier, et al., "Fabrication of porous substrates: A review of processes using pore forming agents in the biomaterial field", J Pharma Sci., 97(3):1135-54 (2008).
Dhariwala, et al., "Rapid prototyping of tissue-engineering constructs, using photopolymerizable hydrogels and sterolithography", Tissue Eng., 10:1316-22 (2004).
Dubruel, et al., "Porous Gelatin Hydrogels: 2. In vitro cell interaction study", Biomacromolecules, 8:338-44 (2007).
Golden and Tien, "Fabrication of microfluidic hydrogels using molded gelation as a sacrificial element", Lab Chip, 7:720-5 (2007).
Linder, et al., "Water-soluble sacrificial layers for surface micromachining", Microfabication, 7:730-6 (2005).
Ling, et al., "A cell-laden microfluidic hydrogel", Lab Chip., 7:756-62 (2007).
Ma and Choi, "Biodegradable polymer scaffolds with well-defined interconnected spherical pore network", Tissue Eng., 7(1):23-33 (2001).
Nahmias, et al., "Laser-guided direct writing for three-dimensional tissue engineering", Biotech Bioeng.,92:129-36 (2005).
Toohey, et al., "Self-healing materials with microvascular networks", Nature Mat., 6:581-5 (2007).
White, et al., "Autonomic healing of polymer composites", Nature, 409:794-7 (2001).

* cited by examiner

Figure 1A      Figure 1B      Figure 1C

PH-SENSITIVE SACRIFICIAL MATERIALS FOR THE MICROFABRICATION OF STRUCTURES

CROSS REFERENCE TO RELATED APPLICATIONS

This application claims benefit of U.S. Provisional Application No. 61/448,432, filed Mar. 2, 2011, which is hereby incorporated by reference in its entirety.

STATEMENT REGARDING FEDERALLY SPONSORED RESEARCH OR DEVELOPMENT

This invention was made with Government Support under Agreement W911NF-07-D-0004 awarded to Massachusetts Institute of Technology by the US Army Corps of Engineers. The Government has certain rights in the invention.

FIELD OF THE INVENTION

This invention is generally in the field of methods of microfabrication and composite materials made there from.

BACKGROUND OF THE INVENTION

The sacrificial layers that are currently predominantly used for microfabrication processes such as micromachining are almost exclusively inorganic materials, the most commonly used being silica, i.e., silicon dioxide ($SiO_2$). Aqueous hydrofluoric acid (HF) selectively etches $SiO_2$ in the presence of silicon and silicon nitride, among other materials. HF also etches many other materials, including metal oxides and organic polymers. Although some non-silicon based materials, e.g., titanium and aluminum, can be used as sacrificial layers to be removed by an HF etch, the poor selectivity of this etch beyond oxides limits its usefulness with a wide range of relatively fragile microelectronic materials. Further, the toxicity of HF makes it inconvenient and/or hazardous and presents difficult disposal requirements. HF-free etching solutions for aluminum are available, based on mixtures of acids and oxidants, e.g., concentrated phosphoric and nitric acids, hydrogen peroxide, and acetic acid. However, these acids are incompatible with some fragile materials.

Organic polymers, such as poly(imide), poly(methyl methacrylate) (PMMA) and photoresist, have been used as sacrificial layers for micromachining. The removal of poly(imide) films by reactive ion etching (ME) is compatible with most inorganic materials, but RIE has little selectivity in etching most organic materials. Sacrificial layers of photoresist can be removed by dissolution in acetone, or by thermal degradation, but these removal steps are incompatible with many other organic polymers. Photoresists that are used as sacrificial layers are also limited by their thermal sensitivity, that is, the photoresist film becomes insoluble in acetone after extended exposure to high temperatures. Sacrificial layers of photoresist are, therefore generally restricted to systems including only inorganic materials, and to processes having a minimal exposure to high temperatures.

Conventional pore-forming agents have also been used as a means of producing pores and/or channels in a material. These agents are generally introduced by dispersing the agents into the material in which the pores or channels are to be formed. The pore-forming agent can be removed by washing with a solvent, such an aqueous solvent or inorganic solvent (e.g., salt leaching); volatilization of the agent, such as by sublimation or evaporation; and/or melting. However, the pores and/or channels produced by these methods are typically isotropic, not well-defined and reproducibility is difficult to achieve.

There exists a need for sacrificial materials that can be removed without the need for strong acids and/or organic solvents which are toxic and/or for which disposal is difficult. The sacrificial materials should be processable, that is, can be patterned or etched using techniques known in the art, and result in the formation of well-defined and reproducible features.

Therefore, it is an object of the invention to provide methods for microfabricating composite materials using sacrificial materials that can be removed using aqueous solution thus avoiding the use of strong acids and/or organic solvents and resulting in the formation of well-defined and reproducible features.

SUMMARY OF THE INVENTION

Methods for microfabricating composite materials and composite materials prepared there from are prepared by applying a sacrificial material to a substrate using techniques known in the art. The sacrificial material(s) are materials whose solubility can be altered by application of a change in pH, alone or in combination with a stimulus such as temperature, light, pressure, presence or absence of ions, and combinations thereof. In a particular embodiment, the sacrificial material(s) is insoluble at a first pH and soluble at a second pH. Change in pH can be coupled with another stimulus, such as temperature, to increase the rate of removal of the sacrificial material(s). The substrate can be embedded in an embedding material(s) along with the sacrificial material or structure or can be removed prior to embedding the sacrificial material structure in an embedding material(s). Alternatively, the sacrificial material can be freestanding. The sacrificial material can be etched or patterned to create a two-dimensional and/or three-dimensional sacrificial material structure.

The sacrificial material structure can be embedded in a wide range of materials provided the embedding material is not soluble under the conditions in which the sacrificial material is removed. The embedding material can be organic or inorganic, biodegradable or non-degradable, and/or polymeric or non-polymeric. In one embodiment, the embedding material(s) is an organic polymeric material. In a particular embodiment, the embedding material(s) is an organic polymeric material which is degradable.

In another embodiment, the embedding material(s) is a hydrogel. The embedding materials can contain one or more additives that modify one or more properties of the embedding materials, such as degradation properties, porosity, mechanical properties, viscosity, conductive properties, and combinations thereof.

Once the sacrificial material structure is embedded in the embedding material(s) to form the composite material, the sacrificial material structure is removed, for example, by submerging the composite material in a sacrificial bath to remove the sacrificial material structure. Removal of the sacrificial material structure results in the formation of one or more well defined two-dimensional and/or three-dimensional structures within the embedding material. In one embodiment, structure within the embedding material is a series of interconnected channels. The diameter of the channels can vary depending on the particular application. However, typically, the channels have a diameter ranging from 0.1 micron to 10,000 microns, preferably 10 microns to 500 microns, more preferably from 50 microns to 250 microns. The shape of the channels can also vary depending on the shape of the sacrificial material structure. In one embodiment, the channels are tubular in shape, wherein the cross-section of the channels is circular, elliptic, rounded, arched, parabolic, or otherwise curved. However, other shapes can also be used. Fluids, such as liquids or gases, can be flowed in and out of the channels of the composite material. In one embodiment, self-healing materials such as healing agents and/or catalysts are circulated through the interconnected network of channels to repair the embedding material. This can allow for the repair of cracks and/or defects in the embedding material in applications in which maintaining the mechanical strength and integrity of the embedding material is of primary importance.

The composite materials described herein can be used in a variety of applications, such as tissue engineering, where the channels can act as a vascular system to support cells; drug screening, where the channels can be used to deliver drugs to cells in three-dimensional cultures in order to study pharmacokinetics in a biomimetic environment; toxin detection, where cells cultured in a 3D biomimetic environment are exposed to unknowns flowing through the channels, and their responses are monitored to check for cell stress or death; drug delivery, where the channels can increase the surface area of the exposed embedding material and may allow better control of drug delivery parameters, filtrations, and bioseparations.

In another embodiment, the composite materials formed from the methods described herein can be used as a microfluidic device in applications ranging from fluid mixing to structural repair. Specific applications of microfluidic devices include, but are not limited to, sensors, chemical reactors, and fluidic-based computers.

BRIEF DESCRIPTION OF THE DRAWINGS

FIG. 1 is a schematic showing the formation, embedding, and removal of a sacrificial material structure. FIG. 1A shows a two-dimensional structure formed on a substrate, which after removal, results in the formation of non-connected channels. FIG. 1B shows a three-dimensional structure formed on a substrate, which after removal, results in the formation of interconnected channels. FIG. 1C shows the formation of a freestanding three-dimensional structure, which after removal, results in the formation of interconnected channels.

DETAILED DESCRIPTION OF THE INVENTION

I. Definitions

"Sacrificial material", as used herein, refers to a material that is employed as a mechanical placeholder in a microfabrication process. "Sacrificial material structure", as used herein, refers to a structure that is formed from the sacrificial material. The sacrificial material structure is ultimately removed to form the desired mechanical structure.

"Embedding material", as used herein, refers to one or more material used to encapsulate the sacrificial material and/or in which the sacrificial material is embedded.

"Hydrogel", as used herein, refers to a crosslinked network of molecules such as polymers that has an affinity for water, e.g., absorb water, but is not water soluble.

"Organo gel", as used herein, refers to a crosslinked network of molecules such as polymers that has an affinity for an organic solution, e.g., absorbs the organic solution, but is not soluble therein.

"Substrate", as used herein, refers to a material or materials to which the sacrificial material is applied. The substrate can provide support for the structures formed from the sacrificial material. The substrate can be embedded in the embedding material(s) with the sacrificial material or structure, it can be used as the support for the embedding material, or can be removed prior to embedding the sacrificial material structure.

"Water soluble", as used herein, is defined as a solubility of at least one gram/liter in an aqueous solution at a temperature in the range of about 0° C. and 50° C. Aqueous solutions can include small amounts of water-soluble organic solvents, such as dimethylsulfoxide, dimethylformamide, alcohols, acetone, and/or glymes. Methods to detect and/or quantify water solubility are well known in the art.

"Residual material" or "residual polymer", as used herein, refers to the small amounts of sacrificial material that may remain after the sacrificial material is removed. In some applications, residual material can be removed using post-processing steps, such as washing.

II. Materials

A. Sacrificial Materials

The sacrificial material(s) are preferably those materials which are insoluble in a solvent at a first pH and soluble in the solvent at a second pH. In some embodiments, the sacrificial material(s) are alkali-soluble resins. While water or aqueous solvents are the preferred solvents, other solvents can also be used. Suitable materials include, but are not limited to, synthetic polymers such as poly(acrylic acid) and derivatives, poly(meth)acrylates, poly methacrylate-co-methacrylic acid, methacrylic acid-methyl methacrylate copolymers, polysulfonamides, methyl acrylate-methacrylic acid copolymers, polyvinyl acetate phthalate, poly beta amino esters, hydroxyethyl methyl acrylate, polyalkylene oxides such as polyethylene glycol (PEG), Poly(N-isopropylacrylamide), poly(vinyl alcohol), polyphosphazene gels, polypropylene fumarate-co-ethylene glycol), and copolymers thereof. An exemplary poly(ether) is poly(ethyleneglycol), e.g., m-PEG. Poly(ethylene imine) is an exemplary polyamine, and poly(acrylic) acid is a representative poly(carboxylic acid). Water-soluble polymeric species include non-ionic, water-soluble polymers such as polyethylene glycol (PEG), polyvinyl alcohol (PVA), poly(hydroxyethyl methacrylate) (pHEMA), poly(acrylamide), poly(vinyl pyrrolidone) (PVP), poly(ethyl oxazoline).

In some embodiments, the sacrificial material is a Joncryl® (BASF) styrene acrylic resin or emulsion, such as Joncryl® 678 or Joncryl® 690. In other embodiments, the sacrificial material is a Carboset® (Lubrizol) acrylic resin, such as Carboset® 519. In other embodiments, the sacrificial material is a rosin derivative, such as a Pentalyn® (Pinova) synthetic resin, including, but not limited to Pentalyn® 830 (thermoplastic resin based largely on a pentaerythritol ester of modified rosin) and Pentalyn® FC (pentaerythritol ester of maleic anhydride-modified wood rosin).

Natural and derivatized natural polymers can also be used, and include materials such as shellac, chitosan, polysaccharides such as alginate, starch, glycogen, guar gum, locust bean gum, dextran, levan, inulin, cyclodextran, celluloses such as cellulose acetate phthalate, cellulose acetate succinate, hydroxy propyl methyl cellulose phthalate, and hydroxy propyl methyl cellulose acetate succinate (hypromellose acetate succinate), and poly(sialic acid), polypeptide-based gels and proteins such as gelatin and gelatin methacrylate, silk hydrogels, extracellular matrix materials, and fibrin, agarose, hyaluronic acid, pectin, and collagen.

Non-polymeric materials such as stearic acid or other fatty acids or salts thereof may also be used to form the embedding and/or the sacrificial material, depending on solubility.

B. Embedding Material

Any material can be utilized as the embedding material so long as it is compatible with the sacrificial material and is not removable under the same conditions.

In one embodiment, the embedding material is a hydrogel or organogel which is not soluble under the same conditions as the sacrificial material.

Other materials can be incorporated into the embedding material, such as cell culture or growth factors, therapeutic, prophylactic, or diagnostic agents, coloring agents, etc.

III. Methods of Microfabrication

Methods of microfabrication using water soluble sacrificial materials and composite materials prepared there from are described herein. In one embodiment, the sacrificial material or materials are insoluble in a solvent at a first pH and soluble in the solvent at a second pH. In a particular embodiment, the solvent is water or an aqueous solvent. In other embodiments, other stimuli may be used to increase the solubility of the sacrificial materials. Because the sacrificial materials are water-soluble at the second pH, the use of non-aqueous organic solvents can be avoided. Avoiding elevated temperatures, organic solvents, and ions which may be reactive with cells, proteins, or other drugs to be delivered have clear benefits over the prior art methods.

The sacrificial materials can be embedded in one or more embedding materials, such as a hydrogel. Upon removal of the sacrificial material(s), a pattern is created in the embedding material which can be used for a variety of applications, such as drug delivery and tissue engineering. The methods described herein provide a rapid means for creating well defined, reproducible three dimensional features without the need for toxic strong acids and/or organic solvents.

These materials can be removed from the final structure by dissolution with an aqueous solution at a pH at which the material is soluble.

Other stimuli may be used, in addition to or as an alternative to changing the pH, in combination with the aqueous solution, to remove the sacrificial structure. Other stimuli include, but are not limited to, changes in temperature or pressure, application of light, or addition or removal of select ions. Methods for inducing solubilization of materials, such as polymers, in a solvent, such as water, using the absence or presence of metal ions is described in U.S. Patent Application Publication to Linder et al. For example, increasing the temperature can be used in combination with changes in pH to increase the solubility of the sacrificial material at the second pH. These methods are distinguished from methods where the material to be removed is melted or otherwise undergoes a phase change.

A. Methods for Patterning Sacrificial Materials

The sacrificial and/or embedding materials may be formed using a variety of techniques known in the art to create patterned surfaces, such as lithographic patterning of the sacrificial material; melt-spinning, wet-spinning, or electrospinning of the sacrificial material; spin-coating of the sacrificial material; three dimensional (3D) printing of the sacrificial material from solution or melt; robotically controlled deposition (RCD); laser etching; plasma or chemical etching; stereolithography; selective laser sintering; ballistic particle manufacture; fusion deposition modeling; surface and bulk micromachining; and combinations thereof. RCD is described in detail in U.S. Patent Application Publication No. 2004/0226620 to Therriault et al. In some embodiments, the sacrificial material(s) may be applied in layers to create three-dimensional structures.

The sacrificial material may be applied to a substrate which is retained after embedding the sacrificial material structure in an embedding material and removal of the sacrificial material. Alternatively, the substrate may be removed after formation of the sacrificial material structure but before embedding the sacrificial material structure in the embedding material(s). Suitable substrates include, but are not limited to, silicon, silicone elastomers, polytetrafluoroethylene (Teflon®), other machinable or moldable polymers, glass, etc.

In another embodiment, the sacrificial material may be freestanding, that is, formed without the use of a substrate. FIGS. 1A and 1B show sacrificial structures that are formed on a substrate. FIG. 1C show a sacrificial structure that is freestanding, that is, formed without a substrate or after the substrate is removed.

B. Embedding Materials

The sacrificial material can be embedded in any material, including but not limited to, biodegradable and non-degradable materials provided the embedding materials do not dissolve under the conditions used to remove the sacrificial materials, e.g., pH. The embedding materials may be organic or inorganic materials. The embedding materials may be polymeric or non-polymeric. In one embodiment, the embedding material is an organic, polymeric material. In a particular embodiment, the embedding material is a hydrogel. The sacrificial material structure can be embedded in the embedding material(s) in a mold so that upon formation of a gel, the composite material has defined shape.

Preferred sacrificial materials where pH-dependent solubility is the control parameter are shellac and the Eugradit® family of polymers.

The embedding material(s) may contain one or more additives to modify one or more properties of the embedding materials. Suitable additives include, but are not limited to, viscosity modifying agents, crosslinking agents, additives that modify the degradation properties of the embedding materials; additives that vary the mechanical properties of the embedding materials, additives that affect the conducting properties of the embedding materials; and combinations thereof. Electrodes may also be incorporated into the embedding materials. While the process described herein can be used with a wide range of embedding materials, it is particularly well suited for use with hydrogels, because it does not require any harsh treatments to effect dissolution of the sacrificial structure and may therefore be biocompatible. Dissolution upon application of stimuli, such as changes in pH, gives the manufacturer greater control over which materials can be used and what size features can be made (e.g., surface-to-volume issues are minimized). Suitable hydrogel materials include, but are not limited to, gelatin, gelatin methacrylate, agarose, alginate, hyaluronic acid, collagen, silk hydrogels, Matrigel, fibrin, chitosan, poly(2-hydroxyethyl methacrylate) (poly-HEMA), polyethylene glycol diacrylate (PEG-DA), polyethylene glycol dimethacrylates (PEG-DMA), poly(N-isopropylacrylamide) (PNIPAAm), poly(acrylic acid) and derivatives thereof, poly (vinyl alcohol), polypeptide-based gels, polyphosphazene gels, poly(propylene furmarate-co-ethylene glycol), and copolymers thereof. Other non-hydrogel materials include polydimethylsiloxane (PDMS), epoxy, polydicyclopentadiene, polycaprolactone and other biodegradable polymers.

C. Sacrificial Bath Solutions

As discussed above, the sacrificial material(s) can be removed by changing the pH to a pH at which the sacrificial material(s) is soluble. Sacrificial bath solutions can be used to change the pH and remove the sacrificial materials. Suitable bath solutions include, but are not limited to, ammonium bicarbonates, borate buffer solutions, phosphate-buffered saline (PBS), ammonium hydroxide, sodium hydroxide, potassium hydroxide, Hank's Buffered Salt Solution (HBSS), standard cell culture media formulations such as Dulbecco's modified Eagle's medium (DMEM) and OptiMEM, (4-(2-hydroxyethyl)-1-piperazineethanesulfonic acid) (HEPES) buffer, tris(hydroxymethyl)aminomethane (TRIS) buffer, pure water, sodium bicarbonate solution, Dulbecco's Phosphate-Buffered Saline (DPBS), Elasmobranch phosphate saline solution (EPBS), and other balanced salt solutions, including custom designed balanced salt solutions.

Generally, the patterned embedding materials, such as patterned hydrogels can be prepared as follows:

(1) A sacrificial structure is formed using one or more pH-sensitive materials. The material(s) are chosen to be insoluble in a solvent in one pH range and soluble in the solvent at another pH range. The material may be patterned using lithographic techniques, by spin-coating a film of the material on a surface (from solution or melt), by spinning fibers of the material, or by using a 3D printer that builds a 3D structure of the material from solution or melt.

2) The embedding material is poured over the sacrificial material structure. The embedding material is chosen to be insoluble in aqueous solution of pH in which the sacrificial material is soluble 3) When the embedding material has solidified or gelled, the composite material is placed in an aqueous bath at a pH in the range in which the sacrificial material is soluble. The composite material is maintained in the bath at a sufficient temperature and for a sufficient time to remove the sacrificial material.

4) Post processing steps, as necessary, can be used to remove residual sacrificial material (clean baths, etc).

The methods described herein provide composite structures having well defined, reproducible features. The features can range in size from as small as nanometers to several millimeters or centimeters, or even larger.

In one embodiment, the sacrificial material structure is substantially removed from the embedding material. "Substantially removed", as used herein, refers to at least 80%, preferably at least 90%, more preferably at least 95%, even more preferably at least 97%, most preferably at least 99% of the total weight of the sacrificial material structure is removed from the embedding material. As discussed above, additional post processing steps can be used to remove any residual sacrificial material if necessary.

D. Self-Repair Materials

The device can be formed of, or include, self-healing materials which are repairable when materials such as a monomer which is a component for the polymer used to make the device is circulated through interconnected channels. Catalyst is embedded within the polymerized "embedding material", so that upon fracture more monomer is exposed to catalyst and it polymerizes itself or another solid gap-filling material to repair the fractured area. Catalysts may be sufficient or act in combination with exposure to light, pH, or other stimuli. This allows for the repair of cracks and/or defects in the embedding material in applications in which maintaining the mechanical strength and integrity of the embedding material is of primary importance.

E. Methods of Making Hydrogel Matrices

IV. Applications of Microfabricated Composite Materials

The patterned composite materials described herein can be used in a variety of applications, particularly medical applications. The ability to make two-dimensional or three-dimensional channels in hydrogels is highly desirable for many applications, including the fields of tissue engineering, where the channels can act as a vascular system to support cells; drug screening, where the channels can be used to deliver drugs to cells in three-dimensional culture in order to study pharmacokinetics in a biomimetic environment; toxin detection, where cells cultured in a 3D biomimetic environment are exposed to unknowns flowing through the channels, and their responses are monitored to check for cell stress or death; drug delivery, where the channels can increase the surface area of the exposed embedding material and may allow better control of drug delivery parameters; filtrations; and bioseparations.

For drug delivery applications, one or more therapeutic, diagnostic, and/or prophylactic agents can be incorporated into the embedding materials. The agents can be released by a number of mechanisms, such as diffusion through the bulk embedding material and/or release through the channels formed by removal of the sacrificial material structure. Active agents include small molecules, such as organic or inorganic molecules having a molecular weight less than 2000 amu and biomolecules, such as peptides, proteins, nucleic acids, and polysaccharides. Suitable classes of active agents include, but are not limited to, analeptic agents; analgesic agents; anesthetic agents; antiasthmatic agents; antiarthritic agents; anticancer agents; anticholinergic agents; anticonvulsant agents; antidepressant agents; antidiabetic agents; antidiarrheal agents; antiemetic agents; antihelminthic agents; antihistamines; antihyperlipidemic agents; antihypertensive agents; anti-infective agents; anti-inflammatory agents; antimigraine agents; antineoplastic agents; antiparkinson drugs; antipruritic agents; antipsychotic agents; antipyretic agents; antispasmodic agents; antitubercular agents; antiulcer agents; antiviral agents; anxiolytic agents; appetite suppressants (anorexic agents); attention deficit disorder and attention deficit hyperactivity disorder drugs; cardiovascular agents including calcium channel blockers, antianginal agents, central nervous system ("CNS") agents, beta-blockers and antiarrhythmic agents; central nervous system stimulants; diuretics; genetic materials; hormonolytics; hypnotics; hypoglycemic agents; immunosuppressive agents; muscle relaxants; narcotic antagonists; nicotine; nutritional agents; parasympatholytics; peptide drugs; psychostimulants; sedatives; sialagogues, steroids; smoking cessation agents; sympathomimetics; tranquilizers; vasodilators; beta-agonist; tocolytic agents, and combinations thereof.

The composite materials formed from the methods described herein can be used as a microfluidic device in applications ranging from fluid mixing to structural repair. Such devices are characterized as having at least one, preferably more than one interconnected channel. The diameter of the channels can vary depending on the particular application. However, typically, the channels have a diameter ranging from 0.1 micron to 1000 microns, preferably 10 microns to 500 microns, more preferably from 50 microns to 250 microns. The shape of the channels can also vary depending on the shape of the sacrificial material structure. In one embodiment, the channels are tubular in shape, wherein the cross-section of the channels is circular, elliptic, rounded, arched, parabolic, or otherwise curved. However, other shapes can also be used. Fluids, such as liquids or gases, can be flow in and out of the composite material through the channels.

Specific applications of microfluidic devices include self-healing materials; sensors, chemical reactors, and fluidic-based computers. Self-healing materials can include circulating through the interconnected network of channels healing agents and/or catalysts to repair (i.e., restore the physical or mechanical or structural properties) of the embedding material. This allows for the repair of cracks and/or defects in the embedding material in applications in which maintaining the mechanical strength and integrity of the embedding material is of primary importance.

This is based on the work of Sottos and White. The healing agent is simply the monomer, and the catalyst is embedded within the polymerized "embedding material", so that upon fracture more monomer is exposed to catalyst and it polymerizes itself. For example, fractures can be filled and/or repaired with a polymerized or crosslinked material a la Sottos and White.

EXAMPLES

Example 1 pH-Sensitive Sacrificial Layer

Shellac was dissolved in methanol at 5% w/v and spun-coated on a silicon wafer at 1900 rpm for 30 seconds. While the film was not optimal (the parameters of the spin-coating, such as solution concentration, solvent, and spin rate, were not optimized), a thin film of shellac was deposited. Gelatin mixed with transglutaminase was pipetted on the wafer, and allowed to crosslink at 37° C. for several hours in a humid environment. The wafer was then placed in a warm 1% ammonium bicarbonate bath, causing the shellac film to dissolve and the gelatin to lift off from the surface.

Example 2 pH-Sensitive 3D Structure Produced by Melt-Spinning for 3D Microfluidics in Hydrogels and Other Materials Using a conventional cotton candy machine, shellac was spun into an interconnected fiber network. This network was placed in a mold made from polydimethylsiloxane, and a solution of gelatin (5% w/v in Hank's Buffered Salt Solution (HBSS)—Ca—Mg) mixed with 1% (w/v total solution) transglutaminase was poured over the shellac structure. The gelatin was allowed to gel for 5 hours in a humid incubator at 37° C. The composite structure was removed from the mold and placed in a bath of 1% (w/v) ammonium bicarbonate in HBSS (—Ca—Mg) at 37° C. After approximately 10 hours, the shellac had dissolved, leaving a fluidic network inside the gelatin. This can be monitored by eye, as the off-white shellac fibers embedded in the gelatin slowly turn transparent.

Example 3 pH-Sensitive 3D Structure Produced by 3D Printing for 3D Microfluidics in Hydrogels and Other Materials Structures were made from molten shellac poured onto aluminum foil by hand in a controlled fashion. The structures were embedded in gelatin in a process similar to that described above, and were sacrificed using the same method (though for a longer time, as the structure size was larger).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:
1. A method of microfabrication of a composite structure having one or more well defined, reproducible two dimensional and/or three dimensional structures, features, or channels each having sizes between nanometers and centimeters comprising
   patterning or etching a sacrificial material formed from a first polymer to form a patterned sacrificial material structure, wherein the patterning or etching of the sacrificial material comprises a method selected from the group consisting of lithographic patterning, melt-spinning, wet-spinning, electrospinning, spin-coating, three dimensional printing, robotically controlled deposition, laser etching, plasma or chemical etching, stereolithography, selective laser sintering, ballistic particle manufacture, fusion deposition modeling, surface micromachining, bulk micromachining, and combinations thereof,
   embedding the patterned sacrificial material structure in a polymeric embedding material to form an embedded sacrificial material structure,
   wherein the patterned or etched first polymer is insoluble in a first solvent at a first pH and soluble in the first solvent upon a change from the first pH to a second different pH,
   contacting the embedded sacrificial material structure with a bath comprising the first solvent at the first pH; and
   changing the first pH of the first solvent to the second different pH, wherein the first polymer is solubilized in the first solvent at the second different pH,
   wherein the polymeric embedding material is not soluble in the first solvent at the second different pH, and
   removing the solubilized first polymer,
   wherein the removal of the first polymer forms the structures, features, or channels, having the pattern of the patterned sacrificial material structure, within the polymeric embedding material.
2. The method of claim 1, wherein the first polymer is water soluble.
3. The method of claim 1, wherein the first polymer is insoluble at low pH and soluble at high pH.
4. The method of claim 3, wherein the first solvent is water.

5. The method of claim 4, wherein the first polymer is selected from the group consisting of shellac, poly(meth) acrylates, methacrylic acid-methyl methacrylate copolymers, chitosan, poly beta amino esters, polysaccharides, polysulfonamides, celluloses, polyvinyl acetate phthalate, stearic acid, gelatin, gelatin methacrylate, agarose, hyaluronic acid, collagen, silk, extracellular matrix material, fibrin, hydroxyethyl methyl acrylate, polyethylene glycol, poly(N-isopropylacrylamide), poly(acrylic acid)s, poly(vinyl alcohol), polypeptide-based gels, polyphosphazene gels, poly(propylene fumarate-co-ethylene glycol), and copolymers thereof.

6. The method of claim 1 comprising forming the composite structure on a substrate.

7. The method of claim 1, wherein the sacrificial material structure or embedding material is a hydrogel.

8. The method of claim 1, wherein the first solvent is selected from the group consisting of ammonium bicarbonate, borate buffer solution, buffered saline, cell culture media, HEPES buffer, TRIS buffer, water, and sodium bicarbonate solutions.

9. The method of claim 1, wherein patterning or etching of the sacrificial material comprises a method selected from the group consisting of lithographic patterning, melt-spinning, wet-spinning, electro spinning, spin-coating, three dimensional printing, robotically controlled deposition, and combinations thereof.

10. A method of microfabrication of a composite structure having one or more well defined, reproducible two dimensional and/or three dimensional structures, features, or channels each having sizes between nanometers and centimeters comprising patterning or etching a sacrificial material formed from a first polymer to form a patterned sacrificial material structure, wherein the patterning or etching of the sacrificial material comprises a method selected from the group consisting of lithographic patterning, melt-spinning, wet-spinning, electrospinning, spin-coating, three dimensional printing, robotically controlled deposition, laser etching, plasma or chemical etching, stereolithography, selective laser sintering, ballistic particle manufacture, fusion deposition modeling, surface micromachining, bulk micromachining, and combinations thereof, embedding the patterned sacrificial material structure in a polymeric embedding material to form an embedded sacrificial material structure, wherein the patterned or etched first polymer is insoluble in a first solvent at a first pH and soluble in the first solvent upon a change from the first pH to a second different pH, contacting the embedded sacrificial material structure with a bath comprising the first solvent at the second different pH; and wherein the polymeric embedding material is not soluble in the first solvent at the first or at the second different pH, and removing the solubilized first polymer, wherein the removal of the first polymer forms the structures, features, or channels, having the pattern of the patterned sacrificial material structure, within the polymeric embedding material.

* * * * *